United States Patent [19]

Schaps et al.

[11] Patent Number: 5,652,389

[45] Date of Patent: Jul. 29, 1997

[54] NON-CONTACT METHOD AND APPARATUS FOR INSPECTION OF INERTIA WELDS

[75] Inventors: Stephen R. Schaps, Tempe, Ariz.; Alfred V. Clark, Boulder, Colo.; Brian Barnes, Tempe, Ariz.

[73] Assignee: The United States of America as represented by the Secretary of Commerce, Washington, D.C.

[21] Appl. No.: 651,597

[22] Filed: May 22, 1996

[51] Int. Cl.$^6$ .......................... G01N 29/04; G01N 29/26
[52] U.S. Cl. .................. 73/643; 73/614; 73/622
[58] Field of Search ............................ 73/602, 609, 610, 73/612, 614, 615, 616, 620, 622, 624, 627, 628, 629, 630, 632, 634, 636, 643; 228/104

[56] References Cited

U.S. PATENT DOCUMENTS

| | | | |
|---|---|---|---|
| 2,782,632 | 2/1957 | Klein et al. | 73/67.2 |
| 3,453,871 | 7/1969 | Krautkrämer | 73/67.8 |
| 3,453,872 | 7/1969 | Botsco | 73/69 |
| 3,460,063 | 8/1969 | Houck et al. | 340/15 |
| 3,564,903 | 2/1971 | Woodmansee et al. | 73/67.2 |
| 3,576,126 | 4/1971 | Weighart | 73/67.7 |
| 3,583,213 | 6/1971 | Houck et al. | 73/67.5 |
| 3,888,114 | 6/1975 | Adams, Jr et al. | |
| 3,926,039 | 12/1975 | Zhukov et al. | 73/67.7 |
| 3,940,952 | 3/1976 | Mitchell | 73/67.8 |
| 4,070,917 | 1/1978 | Niklas et al. | 73/598 |
| 4,122,724 | 10/1978 | Geithman et al. | 73/588 |
| 4,184,374 | 1/1980 | Thompson et al. | 73/640 |
| 4,204,434 | 5/1980 | Whitsel | 73/622 |
| 4,296,486 | 10/1981 | Vasile | 73/643 |
| 4,301,684 | 11/1981 | Thompson et al. | 73/602 |
| 4,366,713 | 1/1983 | Gilmore et al. | 73/618 |
| 4,480,474 | 11/1984 | Kazama et al. | 73/600 |
| 4,680,966 | 7/1987 | Nicolas | 73/597 |
| 5,085,082 | 2/1992 | Cantor et al. | 73/622 |
| 5,121,628 | 6/1992 | Merkl et al. | 73/290 |
| 5,161,413 | 11/1992 | Junker et al. | 73/634 |
| 5,170,929 | 12/1992 | Long et al. | 228/102 |
| 5,303,590 | 4/1994 | Modderman et al. | 73/588 |
| 5,383,365 | 1/1995 | Buttram | 73/598 |
| 5,439,157 | 8/1995 | Geier et al. | 228/9 |
| 5,537,876 | 7/1996 | Davidson et al. | 73/624 |

*Primary Examiner*—Hezron E. Williams
*Assistant Examiner*—Rose M. Miller
*Attorney, Agent, or Firm*—Sheridan Ross

[57] ABSTRACT

The present invention is directed toward a method and apparatus for the non-contact inspection of workpieces having a plate-like portion of the first part joined via an inertia weld to the end of a second part extending away from the plate-like portion. The apparatus and method are particularly apt for the non-contact inspection of driver inflator igniter canisters for airbag applications, such canisters having a spool-shaped structure with outer walls which restrict access to the internal inertia welds for inspection. To achieve non-contact inspection, the invention comprises electromagnetic acoustic transducer means which generate a pulsed inspection signal and a detection signal. In one embodiment, the inspection signal comprises shear acoustic waves which are polarized parallel to the outer surface of the second member (e.g., the central web member of an inflator igniter canister), and a pulse/echo detection approach is employed. Separate electromagnetic acoustic transducer assemblies are utilized to generate the inspection and detection signals, with the transmit assembly being positioned between the detection assembly and workpiece.

20 Claims, 4 Drawing Sheets

NON-CONTACT METHOD AND APPARATUS FOR INSPECTION OF INERTIA WELDS

FIELD OF THE INVENTION

The present invention relates to workpiece inspection and more particularly to the use of electromagnetic acoustic transducer (EMAT) means for non-contact inspection of inertia weld defects. The invention is particularly apt for the inspection of internal inertia welds and web defects in spool-shaped airbag inflator igniter canisters.

BACKGROUND OF THE INVENTION

The inspection of workpieces to detect defects is significantly complicated when the potential defects cannot be identified by visual inspection, and even more particularly, when the location of the potential defects are internal to the workpiece and therefore inaccessible. Such considerations are present with respect to the detection of defects in many products having parts adjoined via an internal inertia weld. Inertia welds are utilized in the production of workpieces to adjoin a plate-like portion of a first part to the end of a second part extending away from the first part, typically in a perpendicular manner.

Specifically, in at least one current airbag inflator igniter canister, a planar "flange" portion of a first shallow cup-shaped member is adjoined via inertia welding to a central, cylindrical "web" member of a second cup-shaped member to yield a closed, spool-shaped structure. The outer walls of the second member obstruct access to the inertia weld formed inside of the canister, as well as the central web member. As a result, and further due to the complex geometry of the canister, it has proven difficult to identify potential defects in the inertia welds and central web member of such canisters.

Prior proposed acoustic-based techniques for inspecting inertia welds generally entail the use of contact transducers that require a gel-based interface with the workpiece or submersion of the workpiece in a liquid. As can be appreciated, both approaches complicate and significantly slow production. Further, when bar codes or other workpiece identification means are utilized on the workpiece, the ability to apply/maintain the integrity of such identification means may be compromised. Additionally, both approaches raise part contamination concerns and may further entail part cleaning/drying.

For inflator igniter canisters, the need to clean/dry canisters following inspection would entail the provision of a heat source. As will be appreciated, such heat sources are avoided in igniter canister production facilities due to the presence of explosive propellants embodied in the finished product. In this regard, it is noted that many ignitor canisters are not currently being individually inspected for inertia weld defects. Rather, a statistically based number of canisters are removed from production and subjected to hydraulic burst testing that destroys the tested canisters.

SUMMARY OF THE INVENTION

Accordingly, it is an object of the present invention to provide an inspection method and apparatus for detecting flaws in inertia welds, and specifically, internal inertia welds utilized in driver inflator canisters for airbag applications. It is an additional object to inspect the entire 360° extent of the internal weld and of the central web member of such canisters for potential defects.

Further objects of the invention are to enhance production efficiencies via "dry" and non-destructive inspection, while maintaining or improving inspection reliability. Related objects include the provision of an inspection system that can be readily implemented in production facilities without major space, power or other facility demands.

To accomplish one or more of the above-noted objectives, the present invention utilizes non-contact electromagnetic acoustic transducer (EMAT) means adjacently positioned in spaced-relation to the workpiece region to be inspected. Such workpiece region includes a plate-like portion, or flange, of a first part adjoined via an inertia weld to the end of a second part that extends away from the flange (e.g., perpendicularly). The non-contact EMAT means generates a pulsed acoustic wave inspection signal in the workpiece that encounters, or is incident upon, the inertia weld. The non-contact EMAT means further detects acoustic waves on the workpiece and generates a detection signal. A processor means compares detection signal-derived values with predetermined values to identify potential defects in the inertia weld and/or second part. By way of example, the predetermined values may correspond with maxima or minima detection signal amplitudes that should be realized for the given workpiece region being inspected in the absence of defects therein.

In one aspect of the invention, the non-contact EMAT means preferably includes two separate non-contact EMAT assemblies (e.g., two separate magnetic coil assemblies) for generating the inspection signal and for detecting acoustic waves and generating the detection signal. This allows for separate tuning of the EMATs and attendant efficiencies. The separate non-contact EMAT assemblies are preferably stacked in co-axial relation to the workpiece region to be inspected, with the transmit EMAT advantageously positioned between the detection EMAT and workpiece. Such arrangement "protects" the detection EMAT from the transmit EMAT inspection pulses.

In a further aspect of the present invention, the inspection signal pulses generated by the non-contact EMAT means in the workpiece are preferably shear acoustic waves that are polarized in a direction substantially parallel to the major surface(s) of the second part extending away from the flange of the first part (as opposed, e.g., to Raighley or compression waves). Such signal pulses may, for example, be generated utilizing an EMAT coil oriented perpendicularly to the major surface of the second part. Further, it is preferable to provide an inspection signal having a frequency that is offset from resonant frequencies of the plate-like flange portion of the first part(e.g., an anti-resonant frequency).

In an additional related aspect of the present invention, it is preferable to utilize non-contact EMAT means having transmission and detection aperture lengths that exceed the thickness of the workpiece region to be inspected, and more particularly, that exceed the width of the inertia weld to be inspected. Where separate transmit EMAT and detect EMAT assemblies are utilized, it is preferable that the transmit EMAT aperture width exceed the detect EMAT aperture width by a factor of at least about 1.5, and more preferably by a factor of at least about 3.0. A wider aperture transmit EMAT advantageously lends to the generation of a collimated acoustic beam in the second part, and the narrower aperture of the detect EMAT yields greater sensitivity for small defects.

In one embodiment directed to the inspection of spool-shaped, aluminum driver inflater canisters for airbag applications, the present invention detects defects in a circular inertia weld adjoining a planar flange to a central, perpendicularly extending tubular web member, as well as defects in the cylindrical web member. Such web member defects may include the absence, incompletion and/or misplacement of intended propellant injection holes passing through the web member (i.e., designed discontinuities).

More particularly, in such embodiment a non-contact, transmit EMAT/detect EMAT assembly is positionable in adjacent, spaced relation to the outside surface of the planar flange closest to the inertia weld. Rotation means are employed to provide relative rotational movement between the igniter canister and the non-contact, transmit EMAT/detect EMAT assembly within a predetermined inspection frame of reference. Such an arrangement allows for progressive, efficient inspection of the entire 360° extent of the inertia weld and cylindrical web member. By way of example, the rotation means may conveniently comprise a turntable upon which the igniter canister is positioned for rotation relative to the transmit EMAT/detect EMAT assembly. In such an arrangement, the EMAT assembly may be advantageously mounted on a reciprocating means that can be advanced for inspection at a predetermined location in the predetermined inspection frame of reference, and retracted for canister loading. Registration means are also provided for registering the angular inspection position of the igniter canister within the predetermined inspection frame of reference, so as to allow for comparison of detection signal-derived values for each given inspected canister portion with corresponding predetermined values stored in a processor means. By way of example, such registration means may include a jig, mounted on a rotatable turntable, and designed to receive an igniter canister in a predetermined angular orientation within the predetermined inspection frame of reference.

It is preferred that a pulse/echo defect detection approach be utilized, wherein the predetermined values that are compared with the detection signal-derived values correspond with detection signal amplitudes that should be realized during predetermined time periods following transmitted inspection signal pulses in the absence of defects. In this regard, for example, with respect to the igniter canister embodiment, inertia weld defects and designed discontinuities in the central web member (e.g., propellant injection holes) will tend to scatter or block incident acoustic wave pulses. Consequently, a value corresponding with the amplitude of a detection signal generated in connection with a predetermined time period, or "window", following an inspection signal pulse can be derived from the detection signal and compared with a predetermined or expected value for a given inspected workpiece region, or "slice", to reveal the presence of defects therein.

Specifically, for example, for a given workpiece region that should not include any designed discontinuity, an inspection signal pulse can be expected to reflect and create an echo pulse that should be detected by a detect EMAT assembly during a predetermined time period to yield a detection signal portion that should have a minimum predetermined amplitude in the absence of an inertia weld defect. Conversely, for a given workpiece region that should include a designed discontinuity, an inspection signal pulse should not create an echo pulse that would be detected by a detect EMAT assembly during a predetermined time period, and therefore the corresponding detection signal should not have an amplitude exceeding a maximum predetermined value in the absence of a defect in the designed discontinuity (e.g., an absent, incomplete or misplaced propellant injection hole in an igniter canister). In this regard, where the presence/absence of designed discontinuities are to be detected in the tubular web member (e.g., propellant injection holes), it is preferred that the width of the transmit EMAT be selected to cover an arc length less than the arc length between such designed discontinuities in the web member. Further, where the transmit EMAT/detect EMAT assembly is positioned adjacent to the top of an igniter canister, it is preferred that at least one predetermined time window be established to provide for the detection of echo pulses reflected at the bottom of the central web member (i.e., at a bottom flange/air interface immediately below and integrally adjoined to the central web member).

Additionally, for current aluminum alloy igniter canisters, it has been determined that the pulsed inspection signal should preferably have a frequency of between about 4 MHz and 6 MHz for pulse/echo detection. Higher frequencies result in greater signal dispersion losses due to aluminum grain size and further cause the inspection signal to become trapped in the inertia weld. Lower frequencies result in greater signal attenuation at the central web/flange interface and are otherwise insensitive to smaller defects.

In another embodiment, a resonance detection approach can be utilized, wherein the frequency of the pulsed inspection signal can be selected to create a resonance within the central web member (i.e., occurring when reflected acoustic waves are in phase with the acoustic waves of the inspection signal). The amplitude of the detection signal will reflect such resonance. Comparison of detection signal-derived values with predetermined values will allow for the detection of defects, since defects will impact the achievement and amplitude of the desired resonance.

As will be appreciated, for both of the pulse/echo and resonance detection approaches, gating means may be advantageously employed in connection with the detect EMAT of the present invention to gate out from the detection signal acoustic waves detected during a predetermined time period following signal transmission by the transmit EMAT. Such gating can effectively deal with coil ring-down following pulsed transmissions, thereby reducing noise and can otherwise provide for selective detection signal processing.

DETAILED DESCRIPTION OF ONE EMBODIMENT

FIGS. 1–4 pertain to the utilization of one embodiment of the present invention for the inspection of air bag driver inflater igniter canisters. As will be appreciated, the invention may be employed in other applications to inspect work pieces having a plate-like first part adjoined via an inertia weld to a second, longitudinally extending part, and particularly, wherein the first and second parts define a structure having a spool-like configuration.

Figure 1:
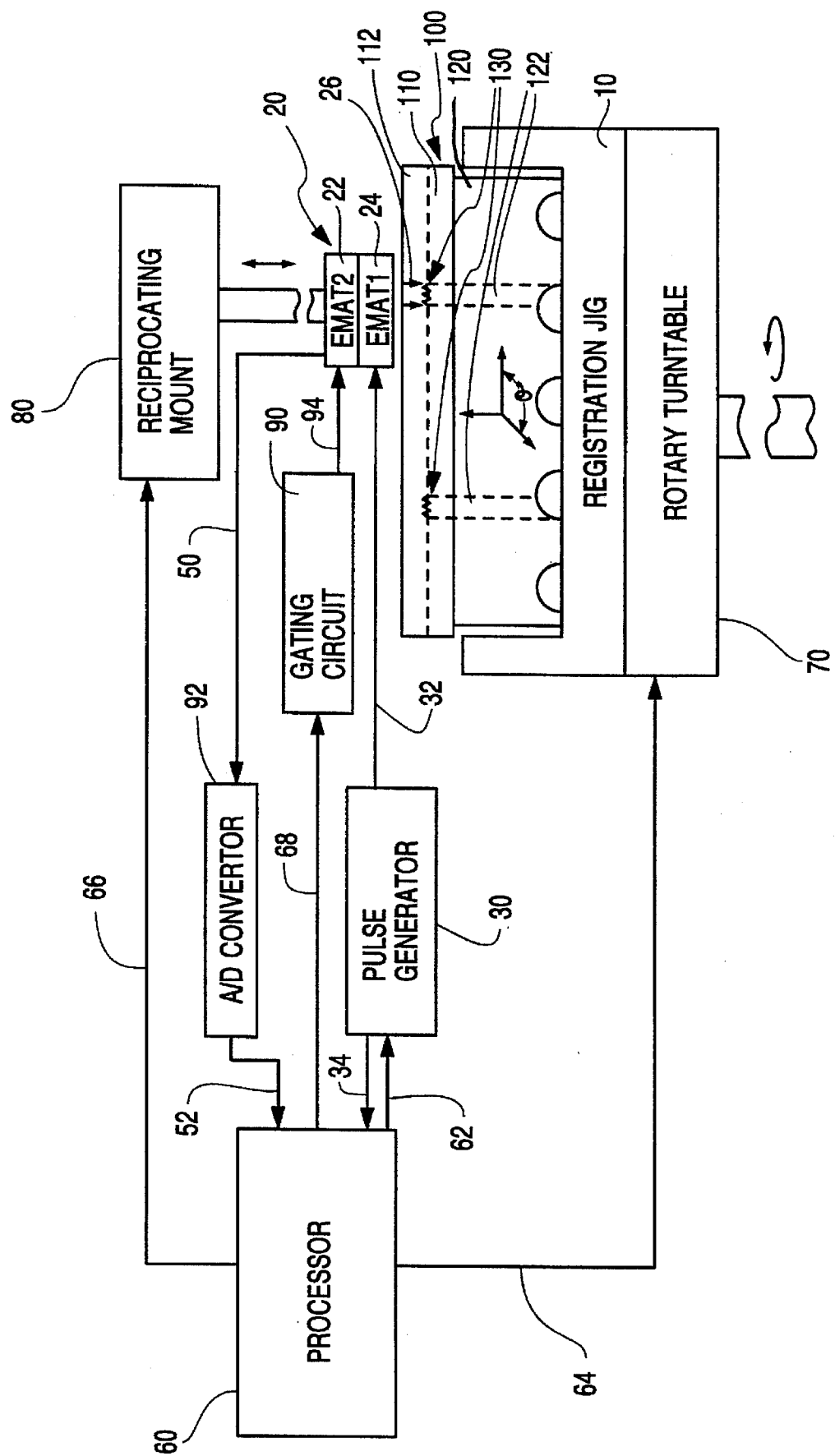
FIG. 1 is a schematic illustration of one embodiment of the present invention employed to inspect an igniter canister.

As shown in FIG. 1, igniter canister 100 is positioned in a predetermined orientation in registration jig 10 within a predetermined frame of reference for inspection by EMAT assembly 20, also positioned in a predetermined position relative to the same predetermined frame of reference. The canister 100 comprises top and bottom parts, 110 and 120, respectively, adjoined via an inertia weld 130 between a plate-like flange 112 of the top part 110 and a tubular central web member 122 integral to the bottom part 120.

EMAT assembly 20 comprises a transmit EMAT1 22 positioned in adjacent, spaced relation relative to the plate-like flange 112, and a detect EMAT2 24 positioned above transmit EMAT1 22. A pulse generator 30 provides a pulsed signal 32 to transmit EMAT1 22 to generate a pulsed acoustic wave inspection signal in the flange 112 of igniter canister 100. The detect EMAT2 24 receives echoed acoustic waves from the flange 112 and generates a detection signal 50. More particularly, e.g., the detection signal 50 will comprise a signal component corresponding with acoustic wave inspection pulses that have been reflected at the air interface of the bottom part 120 underlying the central web member 122 to yield echo pulses detected back at the detect EMAT2 24 within a predetermined "round-trip" time window following the inspection signal pulses.

Gating circuit 90 interfaces with detect EMAT 224 via gating signal 94 to provide detection signal 50 gating. Analog to digital (A/D) convertor 92 receives detection signal 50 and derives amplitude-related values from detection signal 50 to yield a digital detection signal 52. A processor 60 receives digital signal 52 as well as a pulsed signal 34 from pulse generator 30, and compares the amplitude-related values to predetermined values to identify flaws in the inertia weld 130 and/or central web member 122.

To provide for progressive 360° inspection of the inertia weld 130, registration jig 10 is mounted in predetermined angular relation on rotary turntable 70 that rotates the igniter canister 100 in registered relation relative to the EMAT assembly 20. To facilitate loading/unloading of igniter canister 100, the EMAT assembly 20 is mounted on a reciprocating mount 80 that can be selectively advanced downward and retracted upward relative to the igniter canister registration jig 10. For positional coordination and control purposes, processor 60 provides a control signal 62 to pulse generator 30, as well as control signals 64 and 66 to rotary turntable 70 and reciprocating mount 80, respectively. Further, processor 60 provides a control signal 68 to gating circuit 90.

Figure 2:
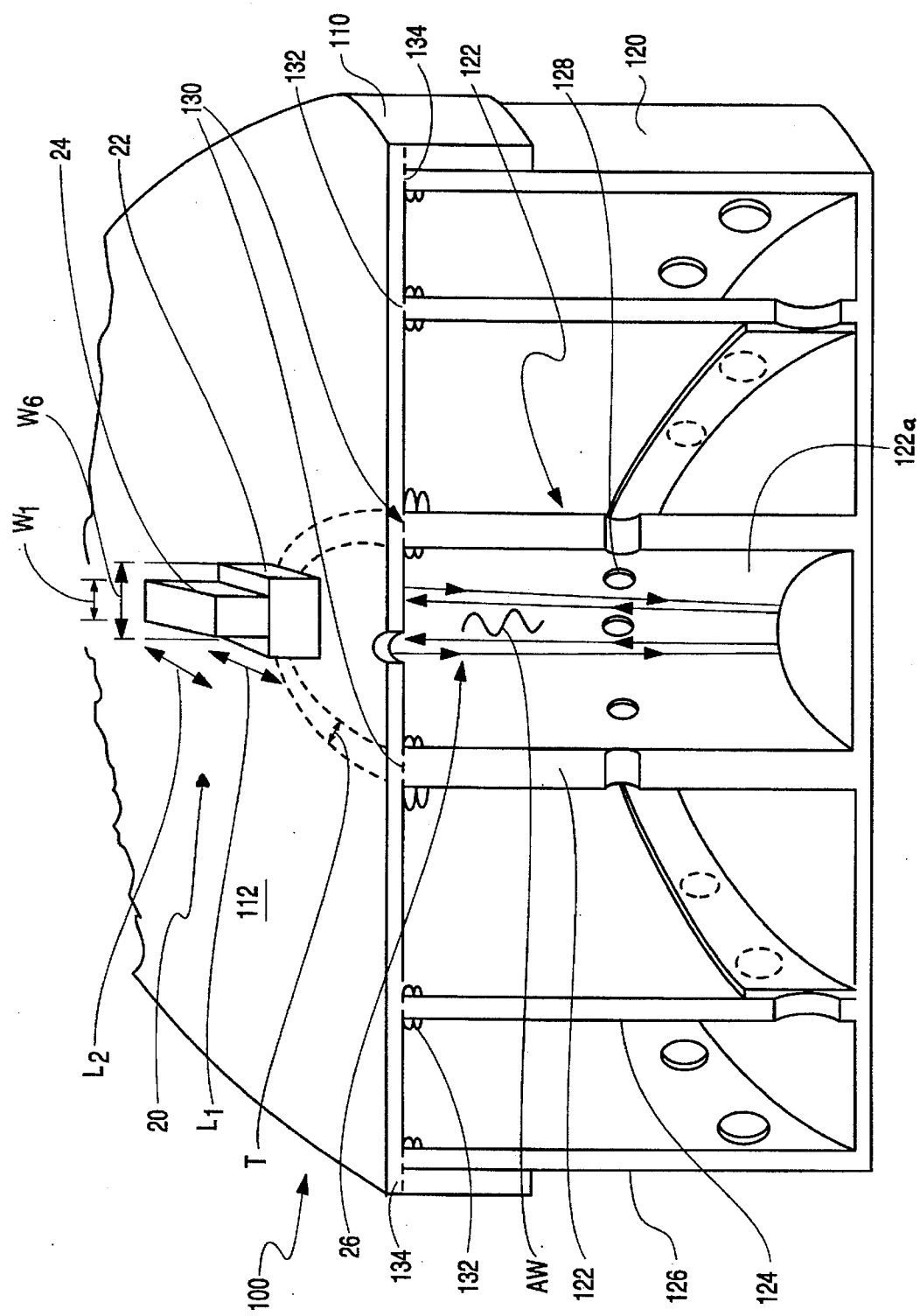
FIG. 2 is a cross-section view of an igniter canister inspected by the embodiment of FIG. 1.

As illustrated in FIG. 2, the top and bottom parts 110 and 120, respectively, of igniter canister 100, are further adjoined via inertia welds 132 and 134 between intermediate wall 124 and outer wall 126 of bottom member 120 and the planar flange 112 of the top member 110, respectively. The central tubular web member 112 includes through holes 128, which present designed-discontinuities, the presence/position of which can be inspected in the described embodiment. In this regard, while the illustrated embodiment is described in relation to the inspection of inertia weld 130 and central web member 172, the present invention can also be employed to inspect inertia welds 132 and 134, and intermediate wall 124 and outer wall 126, respectively.

To carry out the inspection, the transmit EMAT1 22 and detect EMAT2 24 are positioned vertically over and across the inertia weld 130. The length of both the transmit EMAT1 22 aperture $L_1$ and detect EMAT2 24 aperture $L_2$ should exceed the thickness T of the inertia weld 122 to provide sufficient positioning tolerance for production implementation. Further, the width of the transmit EMAT1 22 aperture $W_1$ should exceed the width of the detect EMAT2 24 aperture $W_2$, preferably by a factor of at least about 1.5, and even more preferably by a factor of at least about 3.0.

Figure 3:
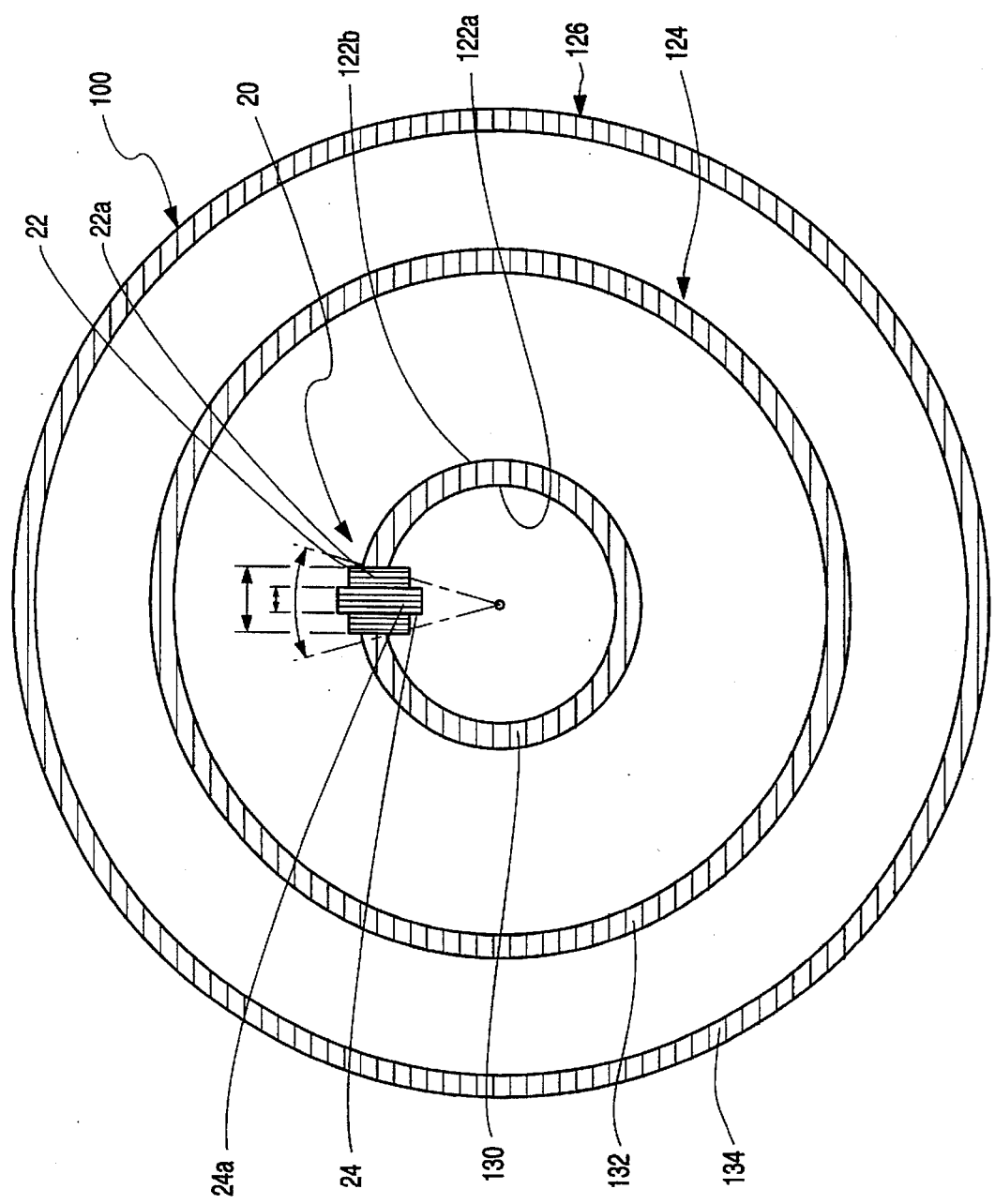
FIG. 3 is a cross-sectional top view of the igniter canister inspected in FIG. 2, with the transmit EMAT/detect EMAT of the embodiment of FIG. 1 superimposed.

The transmit EMAT1 22 generates a pulsed inspection signal 26 comprising substantially collimated acoustic waves AW polarized substantially parallel to the inner and outer walls 122a and 122b, respectively, of the central web member 122. As illustrated in FIG. 3, the acoustic waves AW are generated by orienting the electrically conductive coil 22a of transmit EMAT1 22 substantially perpendicularly to the inner and outer walls 122a and 122b of the central web member 122. For aligned detection purposes, the electrically conductive coil 24a of the detect EMAT2 24 is also positioned in such perpendicular orientation.

The described embodiment produces acoustic waves in the central web member 122 while minimizing acoustic waves in the surrounding planar flange 112, thus minimizing undesired reflections. Further, the disclosed embodiment serves to reduce unwanted reflections from the complex and variable geometry of the weld curl surrounding the inertia weld 130.

The illustrated embodiment has been bench-tested in one application to inspect igniter canisters 100 having an inertia weld 130 and central tubular web member 130 with thicknesses of about 5 mm. In such application, the canisters 100 were inspected utilizing a transmit EMAT1 22 having an aperture size of 10 mm (length) by 10 mm (width) and a detect EMAT2 24 having an aperture size of about 10 mm (length) by 3 mm (width). The web member 130 of the igniter canisters 100 had an outer diameter of about 24 mm and were designed to have eight propellant injection holes 128 of 2 mm diameter each positioned at 45° intervals through and about the central tubular web member 122.

Figure 4A:
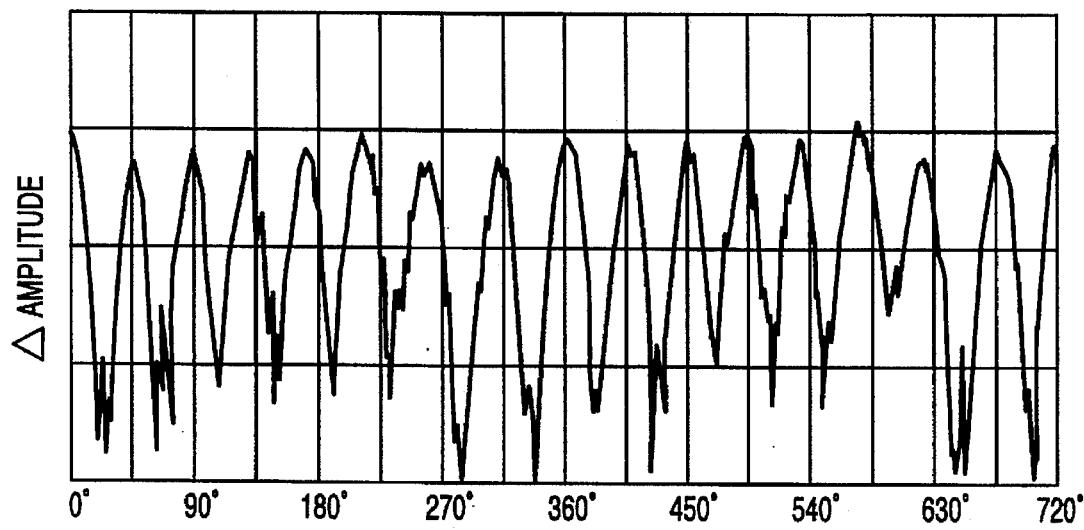
FIGS. 4A–4C illustrate the amplitude of the change ($\alpha$) of a detection signal generated in connection with the embodiment employed in FIGS. 1–3.
Figure 4B:
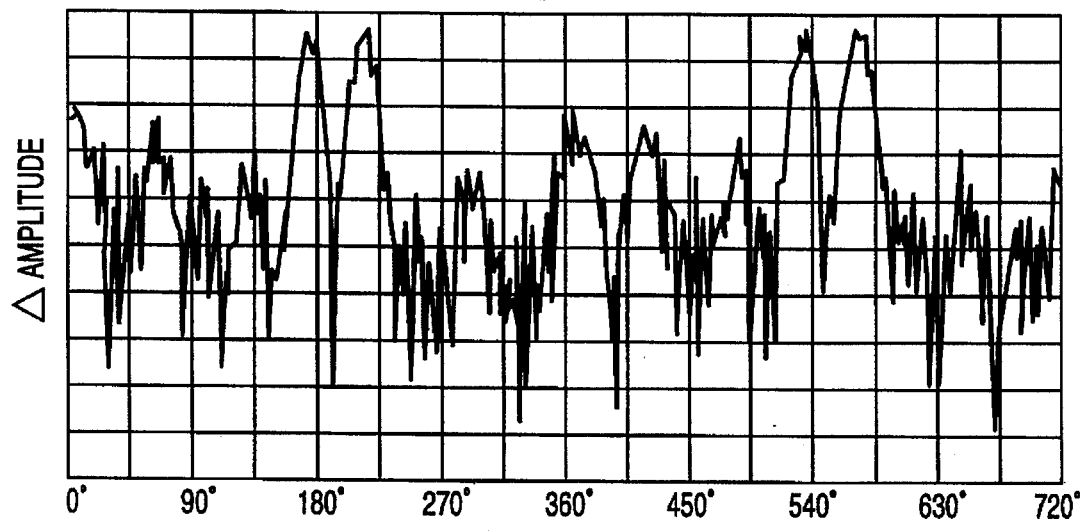
Figure 4C:
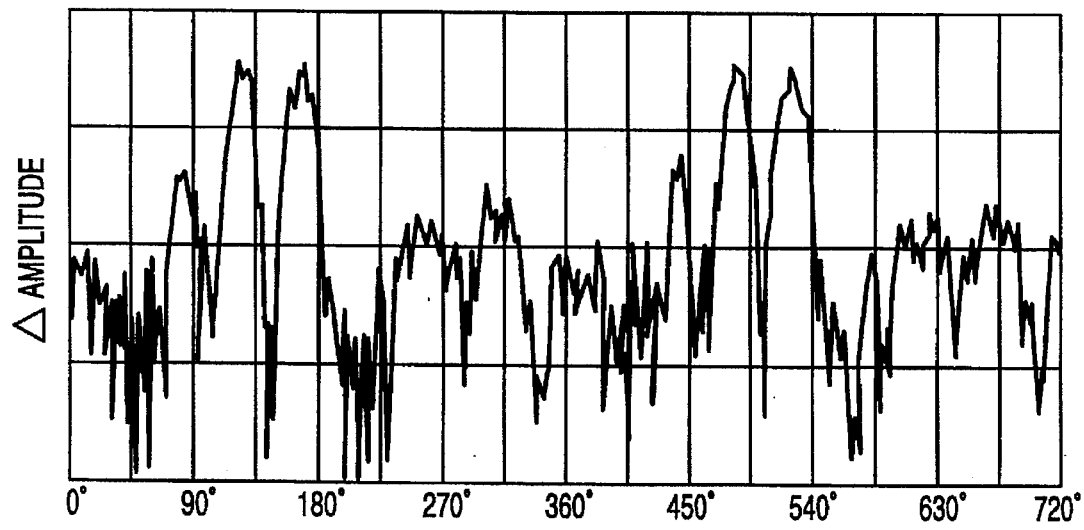

FIGS. 4A–4C illustrate igniter canister angular orientation vs. change in amplitude ($\Delta$) of a pulse/echo detection signal generated utilizing the above-described embodiment for three different igniter canisters inspected in the noted bench testing. As shown, each igniter canister was inspected through two complete rotations (i.e., 720°).

FIG. 4A shows a plot of an igniter canister having no defects. Note the regular sinusoidal-like pattern of maxima and minima. In this case, the maxima amplitudes correspond to those locations where the transmit EMAT1 22 is positioned vertically over a region between the eight through-holes 128 of the central web 122, thereby resulting in a strong detection signal 50 component. For inspection purposes, such maxima amplitudes would, for example, yield detection signal-derived values exceeding a predetermined value, thereby indicating a non-flawed part. The minima amplitude correspond to locations where the transmit EMAT1 22 is positioned directly over through-holes 128, thus resulting in blockage or scattering of incident acoustic waves.

FIGS. 4B and 4C illustrate plots of defective igniter canisters. Specifically, at angular orientations where maxima amplitudes would be detected for a non-defective igniter canister, it can be seen that significant "noise" was experienced, thus yielding detection signal-derived amplitude values below a first predetermined value to indicate the presence of a defective inertia weld. Conversely, and as will be appreciated, for angular orientations where an amplitude minima should be detected (i.e., where propellant injection through-holes should be present), detection signal-derived amplitude values that exceed a second predetermined value will indicate a defective through-hole (i.e., an absent, incomplete or misplaced hole).

The foregoing discussion of one embodiment of the invention has been presented for purposes of illustration and description. The description is not intended to limit the invention to the embodiment described. Variations and modifications commensurate with the above teachings and apparent to those skilled in the art are intended to be within the scope of the present invention.

What is claimed is:

1. An apparatus for inspecting a workpiece having a laterally-extending portion of a first part adjoined by an inertia weld to one end of a second part having an outer surface extending away from the first part, comprising:

electromagnetic acoustic transducer means, positioned in non-contact relation to the workpiece, for generating a pulsed acoustic wave inspection signal incident upon said inertia weld in said workpiece and for detecting acoustic waves in said workpiece and generating a detection signal, said inspection signal including shear acoustic waves polarized in a direction substantially parallel to said outer surface of said second part; and means for utilizing said detection signal to identify defects in said inertia weld by comparing first amplitude-related values derived from said detection signal with first pre-determined amplitude-related values, wherein said first pre-determined amplitude-related values correspond with amplitudes of acoustic wave echo pulses resulting from transmitted inspection signal pulses reflected within said workpiece and detectable by said electromagnetic acoustic transducer means during a first pre-determined time period following transmission in the absence of said defects in said inertia weld.

2. An apparatus as recited in claim 1, wherein said electromagnetic acoustic transducer means comprises an electrically conductive coil for generating said inspection signal, said coil being oriented substantially perpendicular to and across said inertia weld.

3. An apparatus as recited in claim 1, wherein said electromagnetic acoustic transducer means comprises:

a first electromagnetic acoustic transducer assembly for generating said pulsed inspection signal; and a second electromagnetic acoustic transducer assembly for generating said detection signal.

4. An apparatus as recited in claim 3, wherein said first and second electromagnetic acoustic transducer assemblies are stacked in co-axial relation to the workpiece, with the first electromagnetic acoustic transducer assembly being positioned between the second electromagnetic acoustic transducer assembly and the workpiece.

5. An apparatus as recited in claim 3, wherein each of said first and second electromagnetic acoustic transducer assemblies have an aperture with a length exceeding a cross-sectional thickness of said inertia weld.

6. An apparatus as recited in claim 3, wherein said first electromagnetic acoustic transducer assembly has an aperture with a width exceeding the width of an aperture of said second electromagnetic acoustic transducer assembly by a factor of at least about 1.5.

7. An apparatus as recited in claim 1, wherein said means for utilizing compares second amplitude-related values derived from said detection signal with second pre-determined amplitude-related values to identify defects in said second part.

8. An apparatus as recited in claim 1, wherein said electromagnetic acoustic transducer means is positioned adjacent to said plate-like portion of said first part, and wherein said first pre-determined time period is established in relation to a time period for an inspection signal pulse to travel to and be reflected back from an air interface at a second end of said second part for detection by said electromagnetic acoustic transducer means.

9. An apparatus as recited in claim 1, further comprising:

gating means for gating out from said detection signal acoustic waves detected by said electromagnetic acoustic transducer means during a second predetermined time period following transmission of said inspection signal pulses and prior to said first predetermined time period.

10. An apparatus as recited in claim 1, wherein said first pre-determined amplitude-related values correspond with amplitudes of acoustic waves resulting from transmitted inspection signal pulses resonating within said workpiece and detectable by said electromagnetic acoustic transducer means in the absence of defects in said inertia weld.

11. An apparatus for inspecting a workpiece having a laterally-extending portion of a first part adjoined by an inertia weld to one end of a second part having an outer surface extending away from the first part, comprising:

a first electromagnetic acoustic transducer assembly, positioned in non-contact relation to the workpiece, for generating a pulsed acoustic wave inspection signal incident upon said inertia weld in said workpiece;

a second electromagnetic acoustic transducer assembly, positioned in non-contact relation to the workpiece, for detecting acoustic waves in the workpiece and generating a detection signal, said first and second electromagnetic acoustic transducer assemblies being stacked in co-axial relation to the workpiece with said first electromagnetic acoustic transducer assembly being positioned between the second electromagnetic acoustic transducer assembly and the workpiece; and means for utilizing said detection signal to identify defects in said inertia weld.

12. An apparatus as recited in claim 11, wherein each of said first and second electromagnetic acoustic transducer assemblies have an aperture with a length exceeding a cross-sectional thickness of said inertia weld.

13. An apparatus as recited in claim 11, wherein said first electromagnetic acoustic transducer assembly has an aperture with a width exceeding the width of an aperture of said second electromagnetic acoustic transducer assembly by a factor of at least about 1.5.

14. An apparatus as recited in claim 11, wherein said first and second electromagnetic acoustic transducer assemblies include first and second electrically conductive coils, respectively, each of said first and second coils being positioned substantially perpendicularly across said inertia weld, wherein said inspection signal includes shear acoustic waves polarized in a direction substantially parallel to said outer surface of said second part.

15. An apparatus for inspecting a workpiece having a laterally-extending portion of a first part adjoined by an inertia weld to one end of a tubular second part having a cylindrical surface extending perpendicularly away from the first part and having a second end, said cylindrical outer surface having one or more designed discontinuities, comprising:

a first electromagnetic acoustic transducer assembly, positioned in non-contact relation adjacent to said laterally-extending portion of said first part of said workpiece, for generating a pulsed acoustic wave inspection signal in said laterally-extending portion, said first electromagnetic acoustic transducer assembly including an electrically conductive coil oriented substantially perpendicular to said inertia weld, wherein said inspection signal includes shear acoustic waves polarized in a direction substantially parallel to said cylindrical outer surface of said second part;

a second electromagnetic acoustic transducer assembly, positioned in non-contact relation adjacent to said laterally-extending portion of said first part of said workpiece, for detecting acoustic waves in said plate-like portion of said first part and for generating a detection signal, said first and second electromagnetic acoustic transducer assemblies being stacked in coaxial relation to the workpiece with said first electromagnetic acoustic transducer assembly being positioned between the second electromagnetic acoustic transducer assembly and the workpiece; and means for utilizing said detection signal to identify defects in said inertia weld and in said designed discontinuities.

16. An apparatus as recited in claim 15, further comprising:

means for providing relative registered rotation between said workpiece and said stacked first and second electromagnetic acoustic transducer assemblies, wherein a 360° extent of said inertia weld is progressively inspected.

17. An apparatus as recited in claim 16, wherein said means for utilizing compares amplitude-related values derived from said detection signal with pre-determined amplitude-related values to identify said defects, and wherein said predetermined amplitude-related values correspond with amplitudes of acoustic wave echo pulses resulting from transmitted inspection signal pulses reflected within said workpiece and detectable by said second electromagnetic acoustic transducer during predetermined periods.

18. An apparatus as recited in claim 17, wherein each of said first and second electromagnetic acoustic transducer assemblies have an aperture with a width less than a distance between adjacent ones of said designed discontinuities.

19. An apparatus for inspecting a workpiece having a first part with a laterally-extending portion defined by opposing outward-facing and inward-facing surfaces, said inward-facing surface being adjoined by an internal inertia weld to one end of a second part having an outer surface extending away from the inertia weld and away from the inward-facing surface of the laterally extending portion of the first part, comprising:

electromagnetic acoustic transducer means, positioned in spaced, non-contact relation adjacent to an outer surface of the workpiece and in predetermined relation relative to said internal inertia weld, for generating a pulsed acoustic wave inspection signal incident upon said internal inertia weld in said workpiece and for detecting acoustic waves in said workpiece and generating a detection signal, said inspection signal including shear acoustic waves polarized in a direction substantially parallel to said outer surface of said second part; and means for utilizing said detection signal to identify defects in said inertia weld.

20. An apparatus as recited in claim 19, wherein said electromagnetic acoustic transducer means comprises:

a first electromagnetic acoustic transducer assembly for generating said pulsed inspection signal; and a second electromagnetic acoustic transducer assembly for generating said inspection signal, wherein said first and second electromagnetic acoustic transducer assemblies are each positioned on an axis that extends through said second part parallel to the outer surface thereof.

* * * * *